United States Patent [19]

Pertovaara et al.

[11] Patent Number: 5,541,211
[45] Date of Patent: Jul. 30, 1996

[54] ADMINISTRATION OF ATIPAMEZOLE TO ELICIT A YOHIMBINE-LIKE ALPHA-ADRENORECEPTOR ANTAGONISTIC NORADRENERGIC TRANSMISSION

[75] Inventors: Antti Pertovaara, Espoo; Ilkka Linnankoski, Helsinki; Raimo Virtanen, Rusko, all of Finland

[73] Assignee: Orion-yhtyma Oy, Espoo, Finland

[21] Appl. No.: 405,761

[22] Filed: Mar. 16, 1995

Related U.S. Application Data

[63] Continuation of Ser. No. 162,111, filed as PCT/FT92/00191 Jun. 18, 1992 published as WO92/22296 Dec. 23, 1992, abandoned.

[30] Foreign Application Priority Data

Jun. 18, 1991 [GB] United Kingdom .......... 9113077

[51] Int. Cl.⁶ .................................. A61K 31/415
[52] U.S. Cl. ................................ 514/396
[58] Field of Search ........................ 514/396

[56] References Cited

U.S. PATENT DOCUMENTS 4,689,339 8/1987 Karjalainen et al. .

OTHER PUBLICATIONS

"Atipamezole", Drugs Future, vol. 15, No. 5, 1990, pp. 448–452.

"Therapeutic Applications of Drugs Acting on Alpha-Adrenoceptors", E. MacDonald et al., Annals of Clinical Research, vol. 20, 1988, pp. 298–310.

"Increased Sexual Behavior in Male *Macaca arctoides* Monkeys Produced by Atipamezole, a Selective $\beta_2$-Adrenoceptor Antagonist", Ilkka Linnakoski et al., Pharmacology Biochemistry and Behavior, vol. 42, 1992, Pergamon Press Ltd.

*Primary Examiner*—Shep K. Rose
*Attorney, Agent, or Firm*—Burns, Doane, Swecker & Mathis, L.L.P.

[57] ABSTRACT

The present invention is in the art of eliciting a yohimbine-like alpha-adrenoceptor antagonistic noradrenergic neurotransmission male sexual activity response in penile erection. The improvement involves a more rapid onset of action and improved effect than that of yohimbine, consisting essentially of the step of administering the compound atipamezole or a pharmaceutically acceptable acid addition salt thereof to a male in need thereof. Atipamezole or pharmaceutically acceptable acid salt thereof may be administered perorally, intravenously, intramuscularly, transmucosally or transdermally.

12 Claims, 1 Drawing Sheet

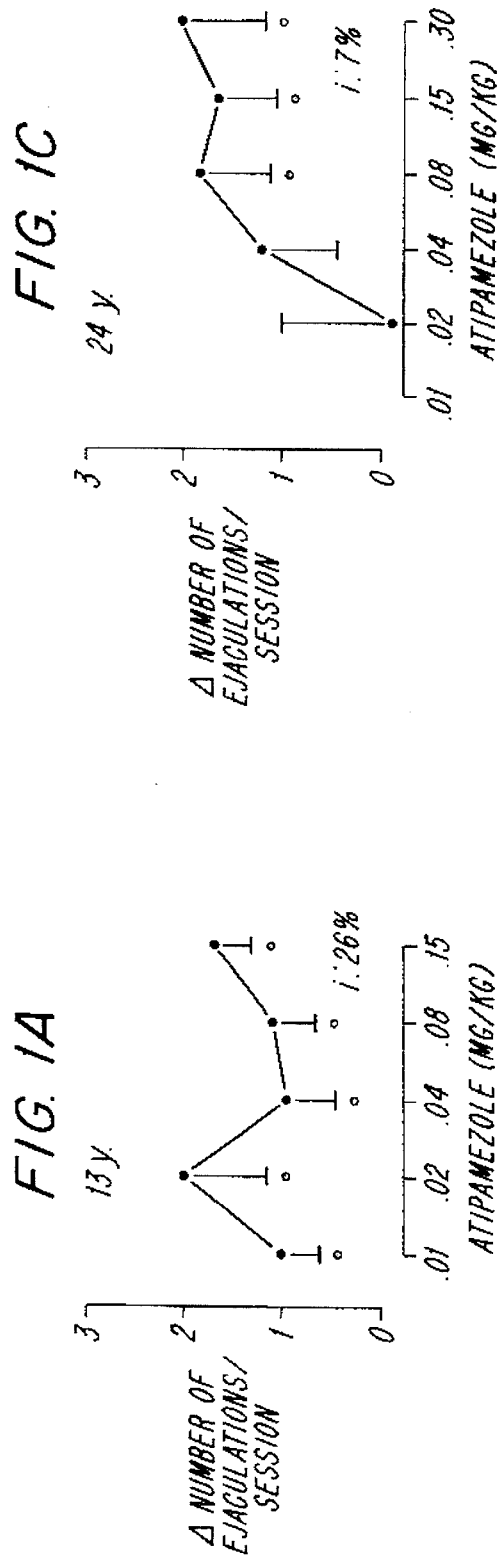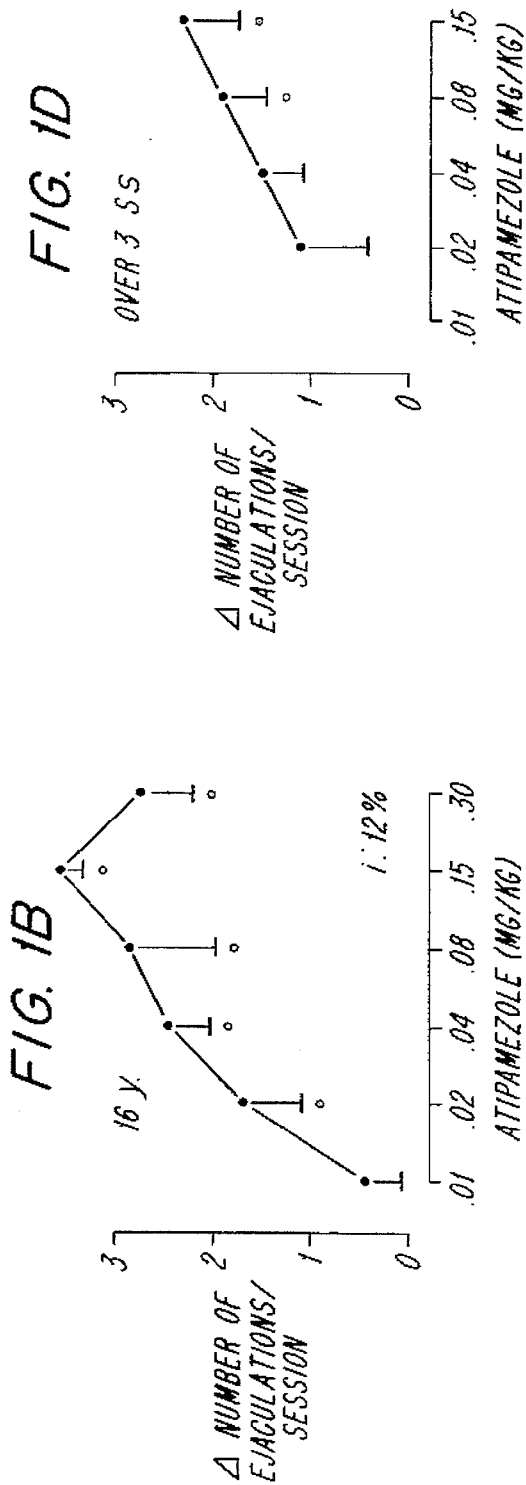

ADMINISTRATION OF ATIPAMEZOLE TO ELICIT A YOHIMBINE-LIKE ALPHA-ADRENORECEPTOR ANTAGONISTIC NORADRENERGIC TRANSMISSION

This application is a continuation of application Ser. No. 08/162,111, filed Dec. 10, 1993, now abandoned. This application was filed in the U.S. as an application under 35 U.S.C. §371 of PCT/FI92/00191, filed Jun. 18, 1992, published as WO92/22296, Dec. 23, 1992, which designated the United States.

This invention relates to a novel therapeutic treatment of male sexual impotence by the administration of atipamezole which is the INN-approved generic name for 4-(2-ethyl-2, 3-dihydro-1H-inden-2-yl)-1H-imidazole or a pharmaceutically acceptable acid addition salt thereof.

Male impotence is a sexual dysfunction relating to difficulties in achieving and/or maintaining sufficient penile erection. It can result from a variety of underlying causes ranging from purely psychogenic to completely physical dysfunctioning. Both surgical and pharmacological therapy have been used in the treatment of impotence. Surgical therapy (implantation of a penile prosthetic device) has been used successfully mainly in the case of a purely organic disease. A variety of agents have been suggested for the use in drug therapy in impotence but the reports of their effectiveness are mainly anecdotal in nature. The use of pharmacological therapy in impotence has thus not gained any wide acceptance so far.

A substantial amount of work has been devoted to identifying the neurotransmitters involved in the facilitation and inhibition of male sexual behaviour (see e.g. Bitran and Hull 1987, Neuroscience and Behavioral reviews 11,365–389). Noradrenergic neuro-transmission seems to have an important role.

Atipamezole is a selective and potent $a_2$-adrenoceptor antagonist which is currently marketed for the reversal of sedative-analgesic veterinary drugs. Atipamezole has been disclosed e.g. in the European Patent EP 183492 as useful for the reversal of detomidine.

We have now found that this compound is also very effective in increasing male sexual capacity in a monkey model. These findings suggest that atipamezole would be an effective therapy in male impotence in humans as well.

Another $a_2$-adrenoceptor antagonist, yohimbine, is currently used for the treatment of male impotence. Yohimbine increases noradrenergic neurotransmission and has been reported to facilitate the sexual capacity of male animals, although the results of different studies are conflicting. Atipamezole is, however clearly advantageous over yohimbine for this use because of its excellent selectivity. The $a_2/a_1$ selectivity ratio of atipamezole is 200–300 times higher than that of yohimbine.

Experimental

Three male and one female stumptail macaques (Macaca Arctoides) were studied in the experiments. The ages of the males were 13, 16 and about 24 years. The age of the female was 6 years.

During the testing period the couple being tested was housed in a single cage (0.6×0.9×1.2 m) with two compartments. Between the sessions and during the first 10 min of each session a sliding wall separated the male and the female in the test cage. The sliding wall was made of iron bars. The monkeys could see and touch each other through the sliding wall. After the i.m. administration of the studied drug dose/saline control to the male, the observation of the sexual behaviour began as described below. Ten minutes after the drug administration the sliding wall between the male and the female was pulled away, and the observation of sexual activity continued for the next 20 min. At the end of the observation period (=30 min after the drug administration) the sliding wall was replaced. Every time a new couple was being tested, the first three sessions were done as above but without the drug administrations to allow habituation of the couple to each other. These first three sessions were not included in the results.

The time of occurrence and duration of the following behaviour was observed: perineal investigation, mounting, ejaculation, tieing, grooming, direct aggression towards the female, yawns, self-scratching, teeth grinding, shaking of cage and masturbation. In the current report only the number of ejaculations in each session is given, since it gave the most straight forward index of male sexual behaviour. For the same reason, the ejaculations obtained by masturbation and intercourse were pooled in the results.

The experiments were performed once daily seven days a week. Atipamezole was given every other day and saline control during other days. The preliminary results in one monkey indicated that there was no difference in the effect of atipamezole whether it was given every third or other day. Atipamezole doses varied from 0.01 to 0.3 mg/kg (dissolved in saline to get a volume of about 0.2 ml). Each dose was tested 5–15 times in each monkey. Taking into account the saline days, the testing of one dose in one monkey took from 10 days to one month. The order of testing each dose was varied between the monkeys to counterbalance possible serial effects. The difference in the number of ejaculations obtained at a given atipamezole dose and the corresponding saline control days was used as an index of the effect of atipamezole on sexual behaviour. This is how the possible variation in the baseline sexual activity (represented by ejaculations during saline days) could be minimized. The incidence of ejaculations (the percentage of saline days with one or more ejaculations) during saline days was used as an index of baseline sexual activity of each male. One way analysis of variance (ANOVA) and Student's t-test were used in statistical evaluation of the data. P<0.05 was considered to represent a significant difference.

In the saline (=control) conditions the incidences of sexual activity (percentage of sessions with ejaculations produced by copulation and/or masturbation) in the three male monkeys were 7%, 12% and 26%. The oldest male had the lowest and the youngest male the highest incidence of sexual activity in control (=saline) conditions. The sexual activity of the males in saline or atipamezole conditions was not dependent on the estrous cycle of the female.

The results obtained with atipamezole are shown in FIG. 1A–D.

Atipamezole increased the number of ejaculations in a dose-dependent way in all three male monkeys (for each individual; p<0.05, ANOVA; FIG. 1A–C). The lowest effective dose of atipamezole varied from 0.01 to 0.08 mg/kg depending on the individual; the younger the male, the lower the lowest effective dose. The average atipamezole-induced increase of ejaculations over the three males also was dose-dependent and significant (p<0.05 ANOVA; FIG. 1 D). No other behavioral effects produced by atipamezole were observed except increased alertness.

The drug is preferably administered perorally, transmucosally, intravenously, intramuscularly or transdermally. The preferable daily dose range is about 0.01 to 1 mg/kg, preferably 0.05 to 0.3 mg/kg for i.v., i.m., transmucosal or transdermal administration and 0.3 to 10 mg/kg for peroral administration.

We claim:

1. In the art of eliciting a yohimbine-like alpha-adrenoreceptor antagonistic noradrenergic neurotransmission male sexual activity response in penile erection, the improvement being a more rapid onset of action and improved effect than that of yohimbine, consisting essentially of the step of administering the compound atipamezole or a pharmaceutically acceptable acid addition salt thereof to a male in need thereof.

2. A method according to claim 1, wherein an effective amount of atipamezole or a pharmaceutically acceptable acid addition salt thereof is administered to treat male sexual impotence.

3. A method according to claim 1, wherein said atipamezole or a pharmaceutically acceptable acid addition salt is administered perorally.

4. A method according to claim 3, wherein said atipamezole or a pharmaceutically acceptable acid addition salt thereof is administered in a dose range of 0.3 to 10 mg/kg.

5. A method according to claim 1, wherein said atipamezole or a pharmaceutically acceptable acid addition salt thereof is administered intravenously.

6. A method according to claim 5, wherein said atipamezole or a pharmaceutically acceptable acid addition salt thereof is administered in a dose range of 0.05 to 0.3 mg/kg.

7. A method according to claim 1, wherein said atipamezole or a pharmaceutically acceptable acid addition salt thereof is administered intramuscularly.

8. A method according to claim 7, wherein said atipamezole or a pharmaceutically acceptable acid addition salt thereof is administered in a dose range of 0.05 to 0.3 mg/kg.

9. A method according to claim 1, wherein said atipamezole or a pharmaceutically acceptable acid addition salt thereof is administered transmucosally.

10. A method according to claim 9, wherein said atipamezole or a pharmaceutically acceptable acid addition salt thereof is administered in a dose range of 0.05 of 0.3 mg/kg.

11. A method according to claim 1, wherein said atipamezole or a pharmaceutically acceptable acid addition salt thereof is administered transdermally.

12. A method according to claim 11, wherein said atipamezole or a pharmaceutically acceptable acid addition salt thereof is administered in a dose range of 0.05 to 0.3 mg/kg.

* * * * *